(12) United States Patent
Highley

(10) Patent No.: US 6,920,960 B2
(45) Date of Patent: Jul. 26, 2005

(54) LUBRICATION CARTRIDGE FOR A PNEUMATICALLY POWERED SURGICAL INSTRUMENT

(75) Inventor: Brian Highley, Keller, TX (US)

(73) Assignee: Medtronic, Inc., Minneapolis, IN (US)

( * ) Notice: Subject to any disclaimer, the term of this patent is extended or adjusted under 35 U.S.C. 154(b) by 0 days.

(21) Appl. No.: 10/180,470

(22) Filed: Jun. 26, 2002

(65) Prior Publication Data

US 2003/0000774 A1 Jan. 2, 2003

Related U.S. Application Data

(60) Provisional application No. 60/360,332, filed on Feb. 26, 2002, provisional application No. 60/352,609, filed on Jan. 28, 2002, and provisional application No. 60/301,491, filed on Jun. 28, 2001.

(51) Int. Cl.[7] ................................................ F16N 7/30
(52) U.S. Cl. .................... 184/55.2; 184/55.1; 184/6.24; 222/189.09; 433/104
(58) Field of Search ................................ 184/6.14, 6.23, 184/6.24, 50.1, 55.1, 55.2, 58, 59; 222/189.09, 334; 433/104

(56) References Cited

U.S. PATENT DOCUMENTS

| 2,456,270 A | * | 12/1948 | Giwosky et al. ........... 184/55.2 |
| 2,792,073 A | | 5/1957 | Boss et al. |
| 2,850,323 A | * | 9/1958 | Veres .......................... 239/354 |
| 2,878,895 A | * | 3/1959 | Wiley .......................... 184/55.1 |
| 2,977,682 A | * | 4/1961 | Flatray ........................ 433/104 |
| 3,364,576 A | * | 1/1968 | Kern, Jr. ....................... 433/82 |
| 4,218,216 A | | 8/1980 | Sugai et al. |
| 4,310,309 A | | 1/1982 | Favonio |
| 4,721,186 A | | 1/1988 | Fujiwara |
| 5,513,722 A | * | 5/1996 | Foltz .......................... 184/55.2 |

FOREIGN PATENT DOCUMENTS

| EP | 0853925 | 7/1998 |
| FR | 2447460 | 8/1980 |

* cited by examiner

Primary Examiner—David M. Fenstermacher
(74) Attorney, Agent, or Firm—Haynes and Boone, LLP

(57) ABSTRACT

An inline oiler cartridge assembly for a pneumatically powered instrument includes a housing, a first conduit and a second conduit. The housing includes a lower portion removably attached to an upper portion. The lower portion defines an inner cavity and an outer cavity. A source of oil is disposed in the inner cavity. A dry fiber cellulose material is disposed in the outer cavity. The first conduit has a first end for attachment to a source of pressurized air and a second end for attachment to a pneumatically powered instrument. The first conduit passes through a portion of the upper portion of the housing and defines a channel for transmission of the source of pressurized air. The channel is in fluid communication with the inner cavity such that the source of pressurized air draws oil into an air stream for delivery to the pneumatically powered instrument.

6 Claims, 5 Drawing Sheets

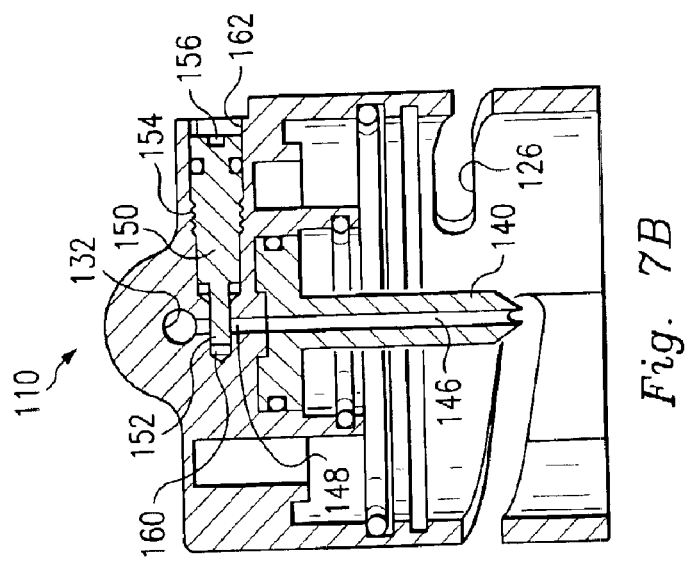
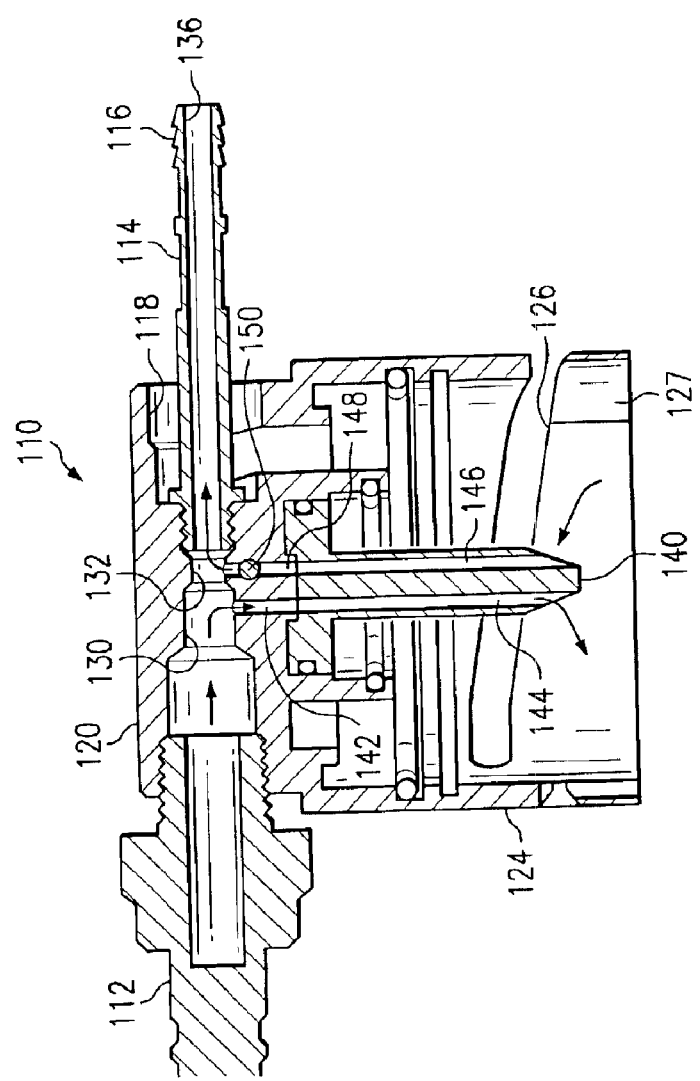

LUBRICATION CARTRIDGE FOR A PNEUMATICALLY POWERED SURGICAL INSTRUMENT

CROSS REFERENCE

The present patent application claims the benefit of U.S. Ser. Nos. 60/301,491 filed Jun. 28, 2001; 60/352,609 filed Jan. 28, 2002; 60/360,332 filed Feb. 26, 2002; and 60/387,626 filed Jun. 11, 2002, all of which are hereby incorporated by reference. The following applications are also related and hereby incorporated by reference: U.S. Ser. Nos. 10/102,762 and 10/135,608.

FIELD OF THE INVENTION

The present invention generally relates to surgical instruments. More particularly, the present invention relates to powered surgical instruments for use in the dissection of bone and other tissue and a lubrication system for use therewith.

BACKGROUND

Doctors and other medical professionals often use powered surgical instruments for dissecting bone and tissue. Often, it is important to lubricate the instruments for proper use. For example, a typical pneumatically powered surgical instrument includes a pneumatic motor connected to a fluid supply source. An oil system is typically place inline between the fluid supply source and the pneumatic motor to provide lubrication to the instrument.

The oil system often must be manually calibrated and/or activated according to predetermined guidelines. For example, the oil system is typically set at a specified drip rate for providing oil into the fluid path. Maintaining the proper drip rate is important to providing the proper amount of lubrication to the instrument. Numerous drawbacks inherently exist in such a system.

SUMMARY

The present invention provides an improved lubrication system for a surgical instrument. In one embodiment, an inline oiler cartridge assembly is provided for a pneumatically powered surgical instrument. The inline oiler cartridge includes a housing, a first conduit and a second conduit. The housing includes a lower portion removably attached to an upper portion. The lower portion defines an inner cylindrical cavity and an outer cylindrical cavity. A source of oil is disposed in the inner cylindrical cavity. An absorbent member is disposed in the outer cylindrical cavity. The first conduit has a first end for attachment to a source of pressurized air and a second end for attachment to a pneumatically powered instrument. The first conduit passes through a portion of the upper portion of the housing and defines a channel for transmission of the source of pressurized air. The channel is in fluid communication with the inner cylindrical cavity such that the source of pressurized air draws oil into an air stream for delivery to the pneumatically powered instrument. The second conduit is concentrically arranged with respect to the first conduit and cooperates with the upper portion of the housing to define a path for returning exhaust gases from the pneumatically powered instrument to the outer cylindrical cavity of the lower portion of the housing.

In another embodiment, an inline lubricant cartridge assembly for use with a pneumatically powered surgical instrument is provided. The inline lubricant cartridge assembly includes a housing with first and second portions, the first portion defining a first cavity including a lubricant-soaked absorbent member. A first conduit having a first end for attachment to a source of pressurized fluid and a second end for attachment to a pneumatically powered surgical instrument is also provided. The first conduit passes through the second portion of the housing and defines a channel for transmission of a pressurized fluid stream. The channel is in fluid communication with the first cavity such that the lubricant is drawn into the fluid stream for delivery to the pneumatically powered instrument.

In some embodiments, the inline lubricant cartridge assembly also includes a second conduit concentrically arranged with respect to the first conduit. The second conduit cooperates with the upper portion of the housing to define a path for returning exhaust gases from the pneumatically powered instrument.

In some embodiments, the first portion also defines a second cavity including a relatively dry absorbent member. The second conduit is in fluid communication with the second cavity for passing the exhaust gases through the relatively dry absorbent member.

In another embodiment, a lubricant system for use with a pneumatic surgical instrument is provided. The system includes a first enclosure positioned inline of a pressurized fluid path, the first enclosure sequentially defining a large-diameter chamber and a small-diameter chamber registering with the pressurized fluid path. Also, a second enclosure including a lubricant is provided. A first fluid path is provided, having a first fluid inlet registering with the large-diameter chamber and a first fluid outlet registering with the second enclosure. A second fluid path is also provided, having a second fluid inlet registering with the second enclosure and a second fluid outlet registering with the small-diameter chamber. A pressurized fluid may flow through the first enclosure such that at least a portion of the fluid flows from the large-diameter chamber, through the first fluid path, through the second enclosure, through the second fluid path, and into the small-diameter chamber.

In another embodiment, an inline oiler for use with a pneumatic surgical instrument is provided. The inline oiler includes a first housing having a first hose fitting for connecting to a source of compressed air and a second hose fitting for connecting to the pneumatic surgical instrument. The inline oiler also includes a second housing including an oil-soaked absorbent member. The inline oiler further includes a chamber defined by the first housing and including a first inlet for receiving pressurized air from the source, a first outlet for providing a portion of the pressurized air to the second housing, a second inlet for receiving the portion of the pressurized air and a predetermined amount of oil from the second housing, and a second outlet for providing the pressurized air, including the portion from the second housing and the predetermined amount of oil, to the surgical instrument.

It should be understood that the present summary and the following detailed description, while indicating the preferred embodiment of the invention, are intended for purposes of illustration only and are not intended to limit the scope of the invention beyond that described in the claims.

BRIEF DESCRIPTION OF THE DRAWINGS

The present invention will become more fully understood from the detailed description and the accompanying drawings, wherein:

FIG. 7A is a cross-sectional view of another embodiment of the present invention.

FIG. 7B is a cross-sectional view of the embodiment shown in FIG. 7A rotated 90°.

DETAILED DESCRIPTION

Figure 1A:
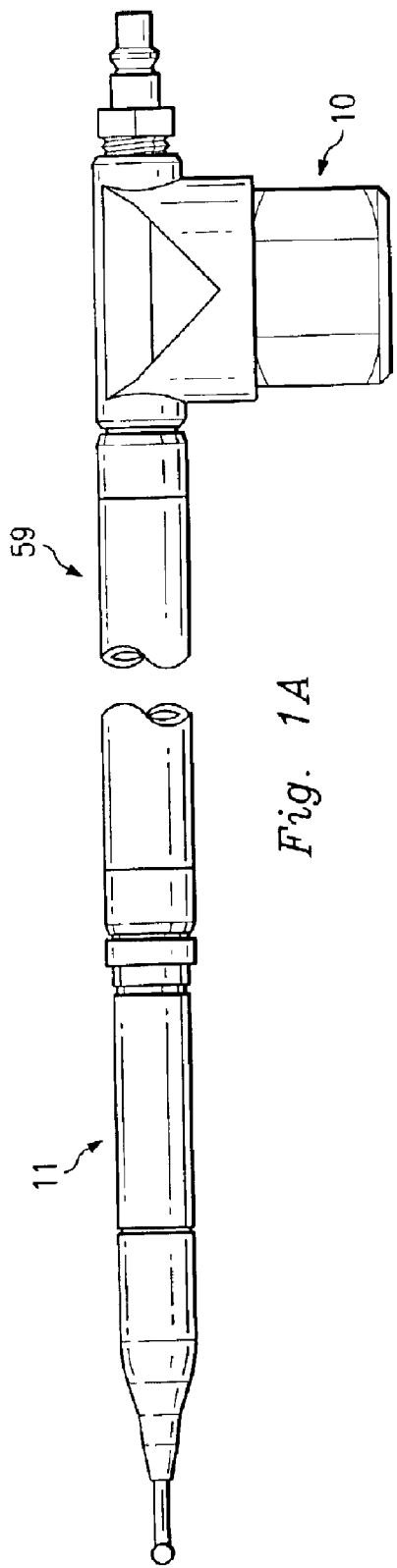
FIG. 1A is an environmental view illustrating an inline oiler cartridge assembly for a pneumatically powered instrument according to the teachings of a preferred embodiment of the present invention shown operatively coupled to a pneumatically powered instrument.

The following description of the preferred apparatus and method of the present invention is merely exemplary in nature and is in no way intended to limit the invention, its application, or uses. Also, it will become apparent to those skilled in the art that the subject invention is not limited to any particular surgical application but has utility for various applications in which it is desired to dissect bone or other tissue, including:

1. Arthroscopy—Orthopaedic
2. Endoscopic—Gastroenterology, Urology, Soft Tissue
3. Neurosurgery—Cranial, Spine, and Otology
4. Small Bone—Orthopaedic, Oral-Maxiofacial, Ortho-Spine, and Otology
5. Cardio Thoracic—Small Bone Sub-Segment
6. Large Bone—Total Joint and Trauma
7. Dental With initial reference to FIGS. 1A and 1B, an inline oiler cartridge assembly for a pneumatically powered surgical instrument according to the teachings of a preferred embodiment of the present invention is illustrated and generally identified at reference numeral 10. In one particular application, the inline oiler cartridge assembly 10 of the present invention is used with a pneumatically powered surgical instrument 11. A suitable surgical instrument is shown in commonly assigned U.S. Pat. No. 5,505,737 which is hereby incorporated by reference as if fully set forth herein. However, it will become apparent below that the teachings of the present invention have applicability for various other powered instruments.

Figure 1B:
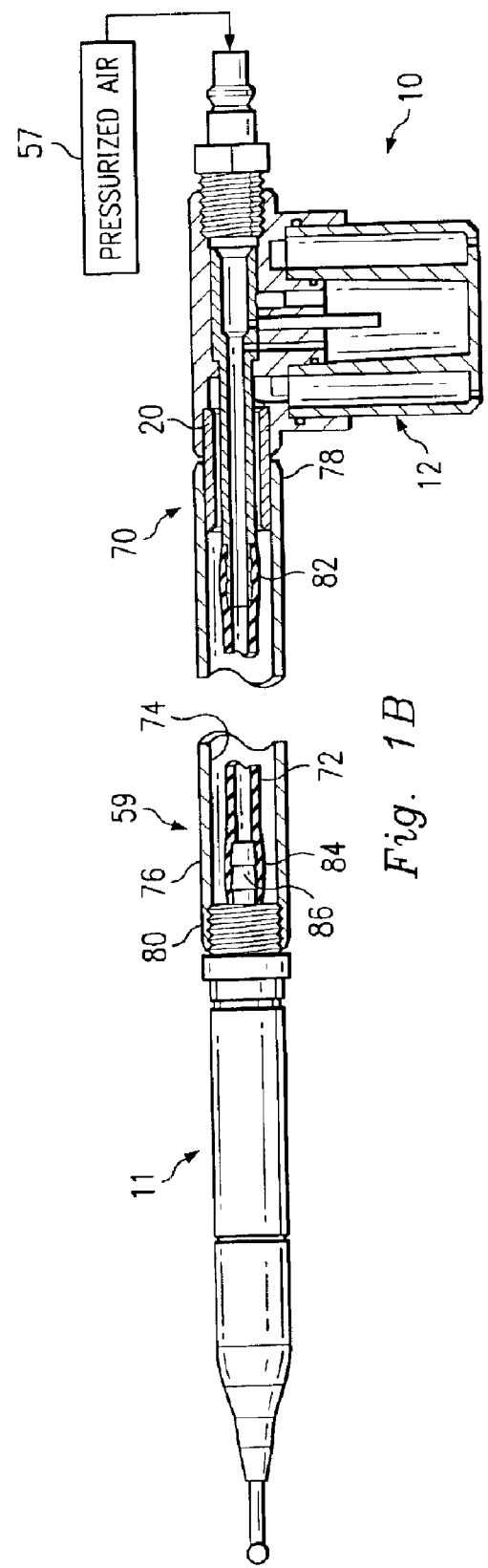
FIG. 1B is a cross-sectional view taken through the arrangement of FIG. 1A, the pneumatic instrument shown in simplified form.

With continued reference to FIGS. 1A and 1B and additional reference to FIGS. 2, 3, 4A–4F, 5A–5D and 6A–6B, the inline oiler cartridge assembly 10 of the present invention will be further described. As perhaps most clearly shown in the exploded view of FIG. 3, the inline oiler cartridge assembly 10 is shown to generally include a body or housing 12 having an upper portion 14 and a lower portion 16. The inline oiler cartridge assembly 10 is further shown to generally include a first conduit 18 for delivering a source of pressurized air to the pneumatically powered instrument 11 and a second conduit 20 for returning exhaust gases from the pneumatically powered instrument 11 to the housing 12 of the assembly 10. Although the first and second conduits 18, 20 are coaxial in the present description, it is understood that in other embodiments, these conduits may be separate (not coaxial), or one of the conduits may not be used at all.

With particular reference to FIGS. 4A–4F, the lower portion 16 of the housing 12 is illustrated to have a generally cylindrical shape. In one application, the lower portion 16 of the housing 12 is injection molded of plastic. Alternatively other suitable materials may be incorporated.

The lower portion 16 of the housing 12 includes an outer cylindrical wall 22, a concentrically arranged inner cylindrical wall 24, and a bottom wall 26. A first generally cylindrical cavity 28 or chamber is defined between the inner and outer cylindrical walls 22 and 24. A second generally cylindrical cavity 30 is defined by the inner cylindrical wall 24.

Figure 4A:
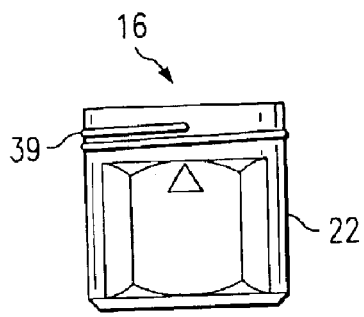
FIG. 4A is a side view of a lower hosing portion of the inline oiler cartridge assembly for a pneumatically powered instrument according to the preferred embodiment of the present invention.
Figure 4B:
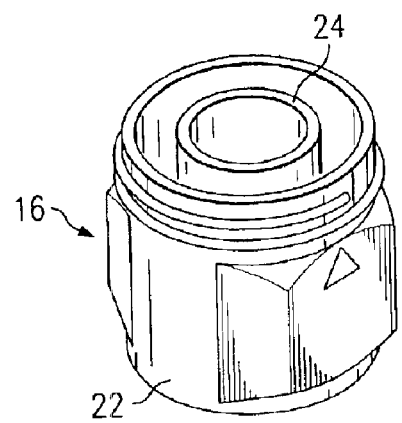
FIG. 4B is a perspective view of the lower housing portion of the inline oiler cartridge assembly for a pneumatically powered instrument according to the preferred embodiment of the present invention.
Figure 4C:
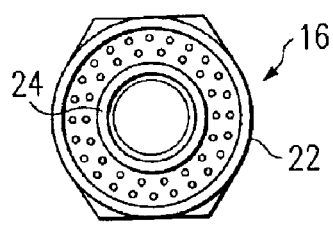
FIG. 4C is a top view of the lower housing portion of the inline oiler cartridge assembly for a pneumatically powered instrument according to the preferred embodiment of the present invention.
Figure 4D:
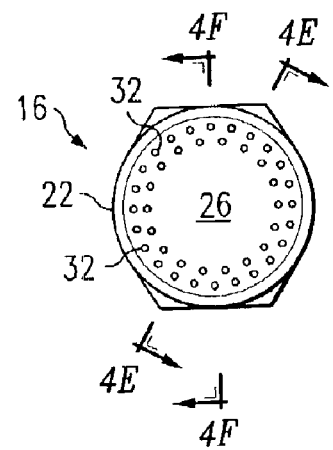
FIG. 4D is a bottom view of the lower housing portion of the inline oiler cartridge assembly for a pneumatically powered instrument according to the preferred embodiment of the present invention.
Figure 4E:
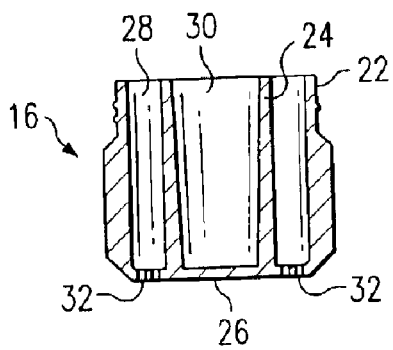
FIG. 4E is a cross-sectional view taken along the line 4E—4E of FIG. 4D.
Figure 4F:
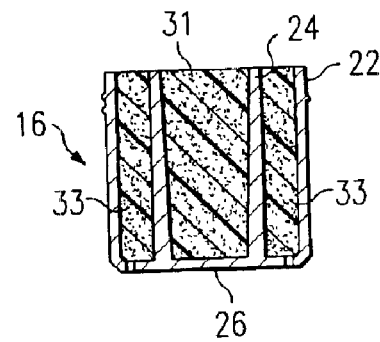
FIG. 4F is a cross-sectional view taken along the line 4F—4F of 4D.

As shown in FIG. 4f, an oil saturated cellulose fiber material 31 is disposed in the second cavity 30. Also, a dry cellulose fiber material 33 is disposed within the first generally cylindrical cavity or lubricant chamber 28. It is understood that cellulose fiber materials 31, 33 are merely examples of absorbent materials, and other examples include foam, wool felt, porous plastics, porous metals and/or other type materials. In a manner to be further addressed below, oil is drawn from the second cavity 30 for introduction into an air stream. Exhaust gases including spent oil are returned to the first cavity 28. The dry cellulose fiber material 33 filters the oil from the exhaust gases. The filtered exhaust gases are permitted to pass through a plurality of exhaust apertures 32 provided in the bottom wall 26 of the lower portion 16.

With particularly reference to FIGS. 5A–5D, the upper portion 14 of the housing 12 will be further described. Similar to the lower portion 16, the upper portion 14 is preferably unitarily constructed of plastic through an injection molding procedure. Again, alternate materials and manners of construction can alternatively be employed.

The upper portion 14 of the housing 12 includes a generally cylindrical segment 36 which is internally threaded. The internal threads 38 engage external threads 39 (FIG. 4A) provided on an upper area of the outer cylindrical wall 22 of the lower portion 16 such that the upper and lower portions 14 and 16 can be removably secured. An upper segment 40 of the upper portion 14 defines a channel 42. A cylindrical portion 44 downwardly extends from the upper segment 40 and into the cavity 30 (FIG. 4E).

The portion 44 includes one or more apertures 46A–C for providing fluid communication between the channel 42 and the cavity 30 and securing the conduit 18. It is understood that there may be several different configurations and sizes of apertures to achieve different results, depending upon the lubrication requirements of the surgical instrument 11. In the present embodiment, the smallest aperture 46A allows inward air pressure to feed into the lubricant chamber 28 thereby pressurizing the lubricant chamber 28. The middle aperture or central aperture 46B projects into the lubricant soaked media of the second cavity 30 and allows lubricant to exit into the air flow passing through the conduit 18. The middle aperture 46B has a larger diameter in order to effect a pressure differential (drop) between the conduit 18 and lubricant chamber 28 thereby creating a Venturi or "sucking" action and drawing lubricant into the air flow passing through the conduit 18 for delivery to the pneumatic motor. As shown in the exploded view of FIG. 3, an oiler tube 48 extends from the central aperture 46B down into the cavity 30. The largest aperture 46C is a hole through which a mechanical securing device (not specifically shown) is positioned for affixing the first conduit 18 to the lubricant chamber 28, as discussed in greater detail below.

Figure 3:
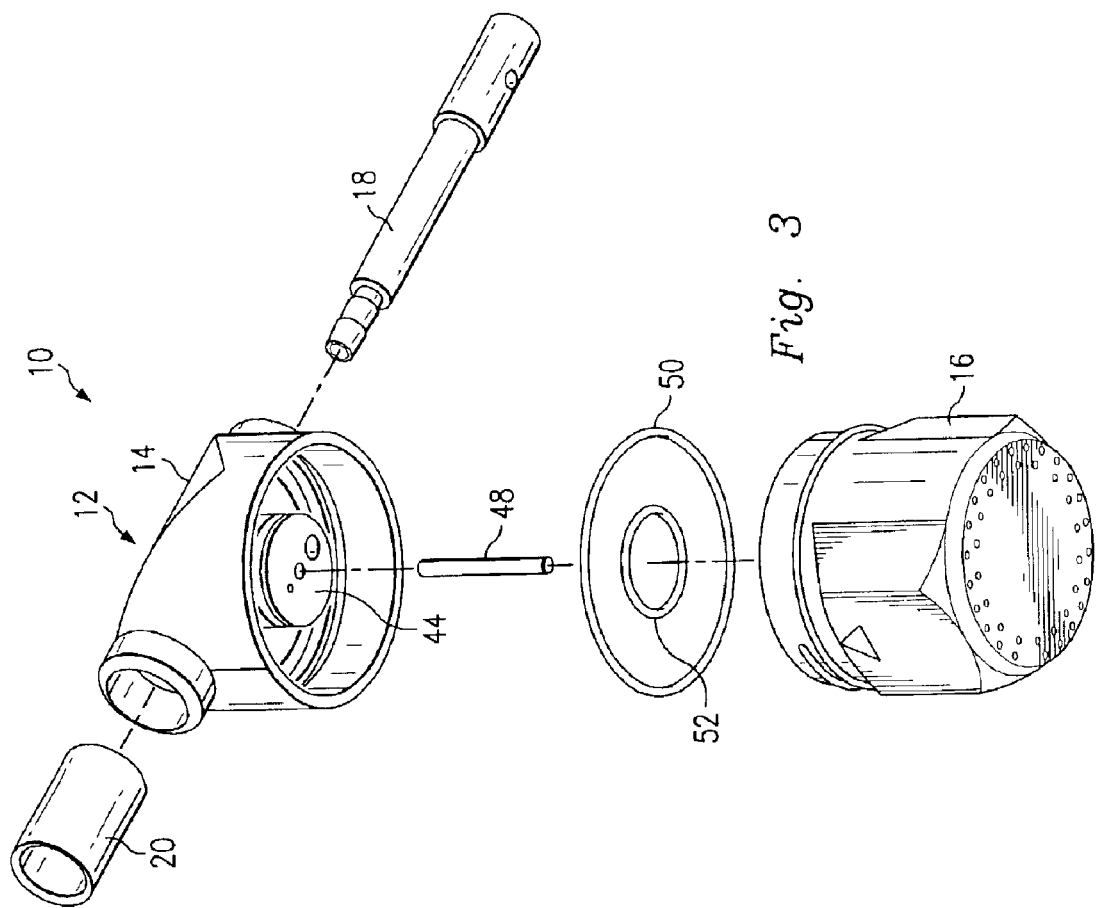
FIG. 3 is an exploded view of the inline oiler cartridge assembly for a pneumatically powered instrument according to the teachings of the preferred embodiment of the present invention.

As particularly shown in FIG. 3, suitable O-rings or gaskets may be employed. Explained further, a first O-ring 50 provides a seal between the upper portion 14 and the lower portion 16 of the housing 12. A second O-ring 52 provides a seal between the cylindrical portion 44 and the chamber 30.

Figure 5A:
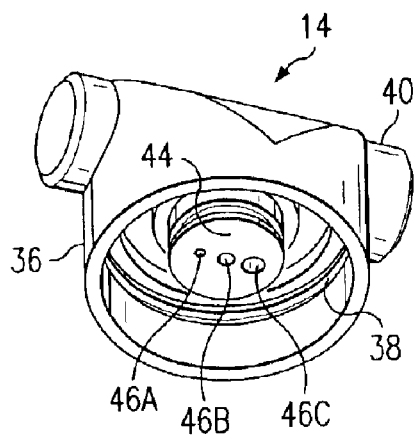
FIG. 5A is a perspective view of an upper housing portion of the inline oiler cartridge assembly for a pneumatically powered instrument according to the preferred embodiment of the present invention.
Figure 5B:
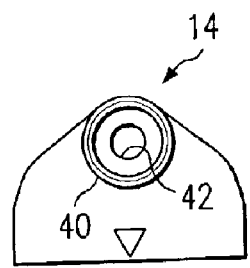
FIG. 5B is a side view of the upper housing portion of the inline oiler cartridge assembly for a pneumatically powered instrument according to the preferred embodiment of the present invention.
Figure 5C:
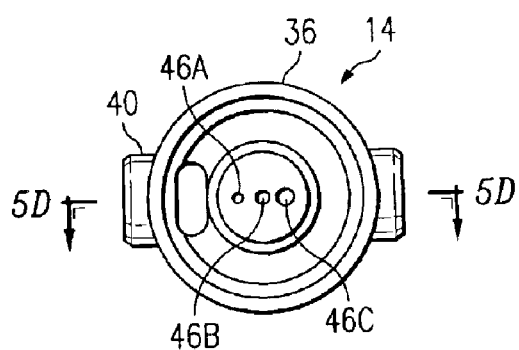
FIG. 5C is a bottom view of the upper housing portion of the inline oiler cartridge assembly for a pneumatically powered instrument according to the preferred embodiment of the present invention.
Figure 5D:
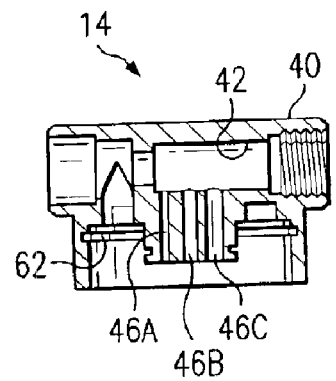
FIG. 5D is a cross-sectional view taken along the line 5D—5D of FIG. 5C.
Figure 6A:
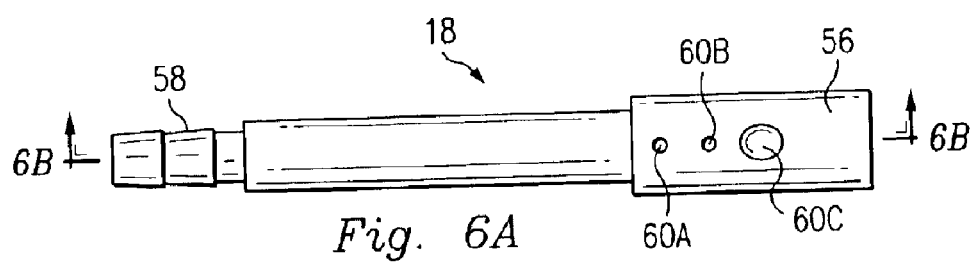
FIG. 6A is a bottom side view of the first conduit of the inline oiler cartridge assembly for a pneumatically powered instrument according to the preferred embodiment of the present invention.
Figure 6B:
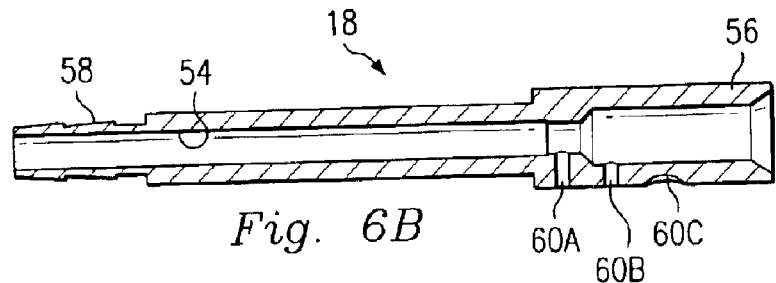
FIG. 6B is a cross-sectional view taken along the line 6B—6B of FIG. 6A.

With particularly reference to FIGS. 6A and 6B, the first conduit 18 of the inline oiler cartridge assembly 10 is further illustrated. The first conduit 18 is a hollow tubular member injection molded of plastic or constructed of other suitable materials. The first conduit 18 defines a central channel 54. A first end 56 of the first conduit 18 is intended to be coupled to an air source (now shown). The first end 56 also is positioned inside of the channel 42 (FIG. 5D). A second end 58 is reduced in diameter and is adapted to be coupled to the pneumatically powered instrument 11 through a hose 59 (FIGS. 1A, 1B). The first conduit 18 includes radially extending apertures 60A–C that align with the apertures 46A–C, respectively, of the upper portion 14 of the housing 12. The mechanical securing device (not shown), such as a set screw, engages with the apertures 46C and 60C to secure the first conduit inside the upper segment 40.

Figure 2:
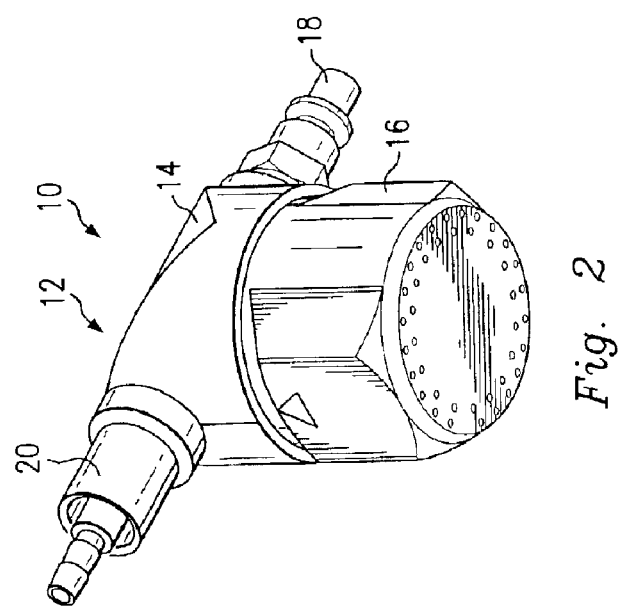
FIG. 2 is a perspective view of the inline oiler cartridge assembly for a pneumatically powered instrument according to the teachings of a preferred embodiment of the present invention.

As particular shown in FIGS. 2 and 3, the second conduit 20 is a hollow tubular member. The second conduit 20 is received within the cylindrical segment 40 of the upper portion 14 of the housing 12 and cooperates with the upper portion 14 to define a fluid path for returning exhaust gases from the pneumatically powered instrument to the outer cylindrical cavity 28 of the lower portion 16. The second conduit 20 concentrically surrounds the second end 58 of the first conduit 18.

In operation, pressurized air is introduced into the first end 56 of the first conduit 18. In one particular application, the air is introduced at a pressure of approximately 120 psi. Further, an on/off control mechanism, such as a foot pedal, may be disposed between a compressed air source and the instrument 11, such as at the first end 56 of the first conduit 18. The pressurized air passes through the channel 54 defined by the first conduit 18 and through a Venturi effect draws oil from the wet fiber cellulose material 31 in the chamber 30 into the air stream. This oil is atomized and delivered with the air stream into the motor of the pneumatically powered instrument for lubrication. On one application, the atomized oil lubricates the motor within approximately 45–50 seconds of startup. This compares with conventional arrangements which take approximately 150 to 300 seconds.

Exhaust gases carrying spent oil from the motor of the pneumatically powered instrument are returned through the second conduit 20. These exhaust gases are introduced into the outer cylindrical chamber 28 containing the dry fiber cellulose material through a pathway 62 (shown in FIG. 5D) defined in the upper portion 14 of the housing 12. The dry fiber cellulose material within the cavity 28 filters the spent oil from the exhaust gases and allows the exhaust gases to pass through the plurality of apertures 32 in the bottom wall 26.

According to a preferred method of the present invention, the inline oiler cartridge assembly 10 described above is pre-filled with oil. The amount of oil is sufficient to ensure lubrication of the motor of the pneumatically powered instrument throughout a surgical procedure. Explaining further, the risk of running out of oil during a surgical procedure is effectively eliminated. After the surgically procedure is completed, the inline oiler cartridge assembly 10 may be disconnected from the surgical instrument and discarded.

Another embodiment of the present invention is illustrated in FIGS. 7A and 7B. Lubrication assembly 110 includes many of the same components of the previously described embodiments and is intended for operation in the same environment set forth above. Lubrication assembly 110 includes a body 120 having apertures for receiving inlet air tube 112 and outlet air tube 114. Preferably, body 120 is formed from aluminum. It will be understood that inlet air tube 112 is connected to a source of pressurized fluid. Further, as shown in FIG. 1B, a coaxial hose may be connected to the lubrication housing 110 with a high pressure hose fitted over flanges 116 and the lower pressure exhaust hose received with aperture 118. Body 120 further defines a cylindrical shell 124 having an opening at one end to receive a lubrication fluid reservoir and exhaust filter unit as previously described above. Shell 124 includes a pair of locking slots 126 adapted to receive projections on the exterior of the lubrication and filter unit to retain it within the body 120. Preferably, internal grooves 127 extend from the aperture opening to the grooves 126 such that the projections may be advanced into the interior of the body 120. It will be appreciated that the helical path of grooves 126 will tend to advance the lubrication and filter unit into the body 120. Grooves 126 includes substantially flat portions at their termination such that the lubrication and filter body will be locked into position in the body 120 and permitting the seals to sealingly engage the lubrication and filter unit.

Lubrication assembly 110 further includes fluid passageways adapted to create fluid flow through the lubrication material (not shown). Specifically, inlet channel 130 having a first diameter is in fluid communication with the pressurized fluid from inlet tube 112. A reduced diameter portion 132 provides a conduit between inlet channel 130 and outlet channel 136 within outlet tube 114. Within the wall defining inlet channel 130, an aperture communicates with inlet fluid path 142. Similarly, within the wall defining reduced diameter portion, an aperture communicates with outlet fluid path 148. A further component of the fluid pathway is extension 140 joined to the body 120 substantially centered within cylindrical shell 124. The extension 140 defines an inlet fluid path 144 in communication with inlet fluid path 142 and an outlet fluid path 146 in communication with outlet fluid path 148. It will be understood that the extension 140 generates a longer fluid path through the lubrication material to enhance the uniform nature of atomizing lubricant in the return air stream.

While it is contemplated that the combination of aperture sizes, fluid passage diameters and lengths may be sized to approximate the desired airflow through the lubricating material, the present embodiment incorporates a flow control mechanism such that air flow may be controlled through the lubricating assembly. Specifically, a needle valve body 150 is received in aperture 162 in the body 120. The needle valve body 150 includes a needle valve portion 152 extending into conical valve seat 160 to restrict fluid flow. The needle valve body 150 also includes an instrument engaging recess 156 to move it within aperture 162 via the threaded connection 154.

The embodiment illustrated in FIGS. 7A and 7B operates in a manner similar to that of the embodiment previously described. By way of example, pressurized fluid entering inlet channel 130 encounters reduced diameter portion 132, thus restricting flow. As shown by the arrows in FIG. 7A, pressurized fluid may enter inlet fluid path 142 and travel through inlet fluid path 144 to exit extension 140 into the lubricant-soaked absorbent material (not shown). As previously described, the absorbent material may be impregnated with oil or some other lubricant. The pressurized fluid tends to seek a path to escape from the lubricant material. As a result of the venturi effect adjacent the aperture in reduced diameter portion 132, outlet fluid path 146 experiences a lower pressure and the higher pressure fluid may flow into the outlet through outlet path 148 and ultimately into reduced diameter portion 132. As the fluid passes through the lubricant material it picks up small particles or drops of lubricant and carries these elements in the fluid stream. The lubricating material may then be carried by the fluid to the motor where it performs its lubricating function. It will be understood that the needle valve 152 may be adjusted to control fluid flow through the lubricating material and thereby control lubricant to the motor. In a preferred embodiment, the needle valve is set in the manufacturing process to provide lubrication within the required specifications prior to packaging and shipping to the end user. It is anticipated that further adjustments will not be necessary for the end user. However, it is contemplated that if changes are made to the lubricating material or the pressure of the inlet fluid, modifications of the needle valve setting may be performed.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An inline lubricant cartridge assembly for use with a pneumatically powered surgical instrument, the inline lubricant cartridge assembly comprising:
    a housing including first and second portions, the first portion defining a first cavity including a lubricant-soaked absorbent member;
    a first conduit having a first end for attachment to a source of pressurized fluid and a second end for attachment to a pneumatically powered surgical instrument, the first conduit passing through the second portion of the housing and defining a channel for transmission of a pressurized fluid stream, the channel being in fluid communication with the first cavity such that lubricant is drawn into the fluid stream for delivery to the pneumatically powered instrument; and
    a second conduit concentrically arranged with respect to the first conduit and cooperating with the second portion of the housing to define a path for returning exhaust gases from the pneumatically powered instrument;
    wherein the first portion also defines a second cavity including a relatively dry absorbent member and wherein the second conduit is in fluid communication with the second cavity for passing the exhaust gases through the relatively dry absorbent member.

2. The inline lubricant cartridge assembly of claim 1 wherein the lubricant-soaked absorbent member is a fiber cellulose material soaked with oil.

3. The inline lubricant cartridge assembly of claim 1 wherein the first portion of the housing is removably attached to the second portion.

4. The inline lubricant cartridge assembly of claim 1 wherein the first end of the first conduit attaches to the source of pressurized fluid through a first detachable hose and the second end of the first conduit attaches to the pneumatically powered surgical instrument through a second detachable hose.

5. A lubricant system for use with a surgical instrument, comprising:

a first enclosure positioned inline with a pressurized fluid path, the first enclosure sequentially defining a large-diameter chamber and a small-diameter chamber for defining at least a portion of the pressurized fluid path, the first enclosure positioned inline of an exhaust path and sequentially defining an exhaust chamber registering with the exhaust path;

a second enclosure including a lubricant and a relatively dry absorbent member;

a first fluid path having a first fluid inlet registering with the large-diameter chamber and a first fluid outlet registering with the second enclosure;

a second fluid path having a second fluid inlet registering with the second enclosure and a second fluid outlet registering with the small-diameter chamber; and a third fluid path having a third fluid inlet registering with the exhaust chamber and a third fluid outlet registering with the relatively dry absorbent member;

whereby a pressurized fluid may flow through the first enclosure such that at least a portion of the pressurized fluid flows from the large-diameter chamber, through the first fluid path, through the second enclosure, through the second fluid path, and into the small-diameter chamber.

6. An inline oiler for use with a pneumatic surgical instrument, comprising:

a first housing including a first hose fitting for connecting to a source of compressed air and a second hose filling for connecting to the pneumatic surgical instrument;

a second housing including an oil-soaked absorbent member;

a first chamber defined by the first housing, the first chamber including a first inlet for receiving pressurized air from the source, a first outlet for providing a portion of the pressurized air to the second housing, a second inlet for receiving the portion of the pressurized air and a predetermined amount of oil from the second housing, and a second outlet for providing the pressurized air, including the portion from the second housing and the predetermined amount of oil, to the surgical instrument;

a second and third chamber defined by the second housing, the second chamber including the oil-soaked absorbent member and the third chamber including a relatively dry absorbent member; and a fourth chamber defined by the first housing, the fourth chamber including an inlet for receiving an exhaust fluid from the surgical instrument and an outlet for providing the exhaust fluid to the relatively dry absorbent member.

* * * * *